United States Patent [19]

Al-Rawi

[11] Patent Number: 4,751,791
[45] Date of Patent: Jun. 21, 1988

[54] DATE PALM POLLINATOR

[76] Inventor: Omar M. A. Al-Rawi, Ameria, Al-Fikdous quarter No. 8/4/630, Baghdad, Iraq

[21] Appl. No.: 15,893

[22] Filed: Feb. 18, 1987

[30] Foreign Application Priority Data

Feb. 23, 1986 [IQ] Iraq ............................................. 39/86

[51] Int. Cl.$^4$ .......................... A01H 1/02; A01G 7/00
[52] U.S. Cl. .................................................... 47/1.41
[58] Field of Search ................. 47/1.41; 239/280–281, 239/532, 375; 222/630, 637; 406/153

[56] References Cited

U.S. PATENT DOCUMENTS

| | | | |
|---|---|---|---|
| 2,802,302 | 8/1957 | Yost | 47/1.41 |
| 3,943,660 | 3/1976 | Hosaka | 47/1.41 |
| 3,962,821 | 6/1976 | Sharp | 47/1.41 |
| 4,678,377 | 7/1987 | Bouchard | 222/630 |

*Primary Examiner*—James R. Feyrer
*Attorney, Agent, or Firm*—Ladas & Parry

[57] ABSTRACT

A plant duster, especially for data palm pollination, has a small tube for dispersing dust and a container for the dust to be dispensed. A rubber stopper in one end of the container and about one end of the small tube flexibly mounts the small tube on the container for communication with the container for receiving the dust. A truncated, hollow cone has one end on the other end of the container for communicating with the dust therein and a threaded tube on the other end. A first carrying tube section is threaded on to the threaded tube at one end and has an enlargement about the other end. There are also further carrying tube sections in graduated diameters, each further carrying tube section having an enlargement about one end corresponding to that about the other end of the first carrying tube section and an expandable connection about the other end for releasibly receiving the enlargement of another carrying tube section. A last carrying tube section has an expandable connection corresponding to those of the further carrying tube sections on one end and threads on the other end. A tubular, battery-operable air pump has threads on one end for connection to the threads on the last carrying tube section for pumping air through connected carrying tube sections to the container, whereby to entrain the dust therein and dispense the entrained dust through the small tube.

4 Claims, 2 Drawing Sheets

U.S. Patent  Jun. 21, 1988  Sheet 2 of 2  4,751,791
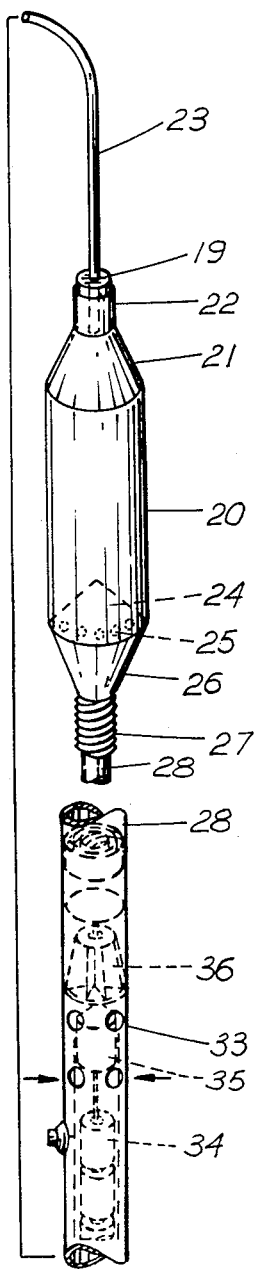
FIG. 4
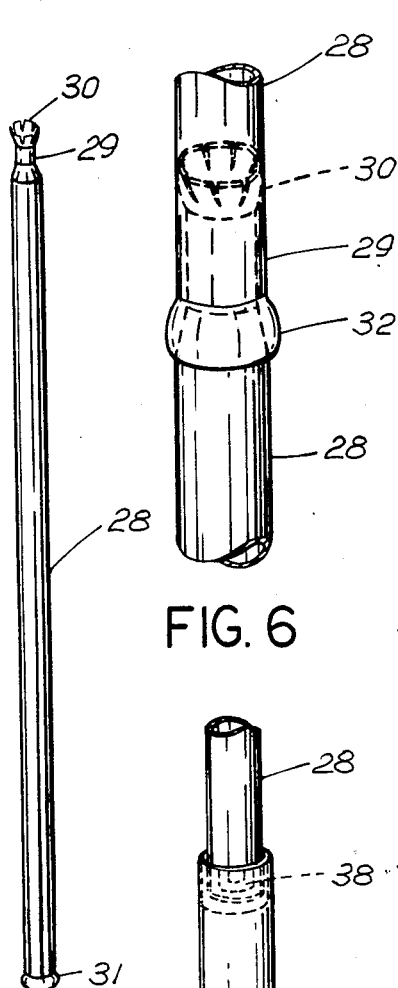
FIG. 5
FIG. 6
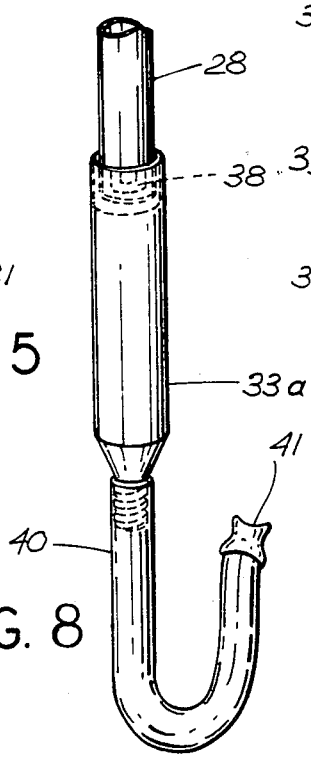
FIG. 8
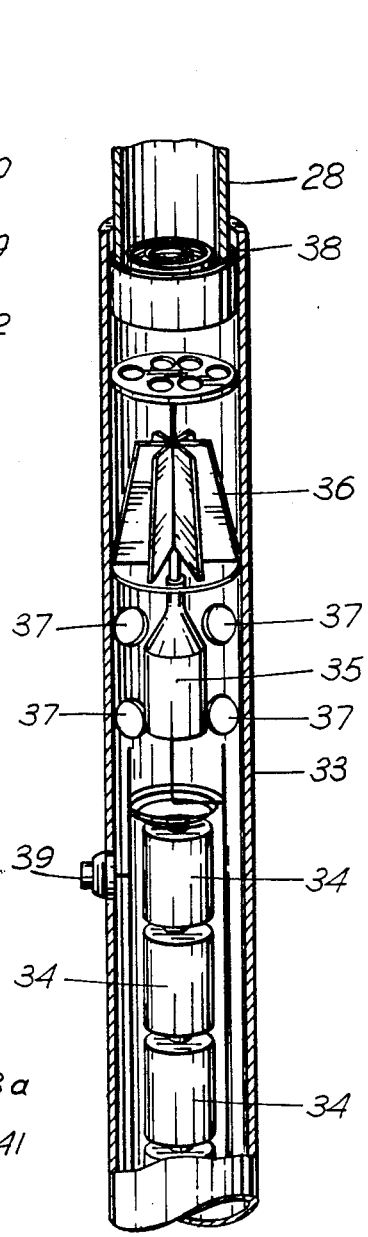
FIG. 7

DATE PALM POLLINATOR

BACKGROUND OF THE INVENTION

The invention relates to a plant duster and, more particularly, a duster for dusting pollen, insecticide or other powder onto a date palm.

The date palm tree is a monosexual and needs transfer of pollen from the flowers of a male tree to the flowers of a female tree to give proper fruit. Such pollen transfer may occur naturally by air, but this way yields little or no fruit. It may also occur manually by taking some of the male flowers to spray their pollen onto the female flowers. This requires climbing up the tree, however, which is very difficult. To make such manual pollen transfer easier, therefore, pollinators are used. Some of the pollinators still require climbing up the tree, like the so-called American and Japanese pollinators, for example. Some of them need heavy machinery or compressed air, like those sold under the marks Al-nahren, Homribi and Baghdad, for example. Some of them are difficult to use in other ways, especially in raising to female flowers at the top of a very high tree.

The inventor named herein has, therefore, also invented pollinators identified as Mosa'ab, Mahmood and Osamah Pollinators to try to avoid the described disadvantage of the other above-identified pollinators. Thus, these require no heavy machinery and no compressed air. They are also cheap and can be raised to the tops of high trees easily. They are also easy to operate.

The Mosa'ab Date Palm Pollinator has a long, graduated aluminum carrying tube. On one, upper end of the carrying tube, there is a small cylindrical container for male pollen with a cone-shaped lower part connecting it, point down, to a horizontal, small-diameter tube, transverse to the carrying tube, for funneling the pollen thereinto. The small-diameter tube is connected at one end to the lumen of the carrying tube and is open at the other end, which projects from the container about 3 cm., to allow the pollen to go out. The lower end of the carrying tube has a small bulb pump of about 50 c.c. capacity. For use, the carrying tube is grasped by hand to position the open end of the small-diameter tube at a female flower. The bulb is then squeezed to pump air into the lumen of the carrying tube and, therefrom, to the connected end to the small-diameter tube to push the pollen dropped thereinto from the container out onto the female flower for pollination.

The Mahmood Date Palm Pollinator has the same carrying tube. Its cylinderical container on one end thereof for pollen also has a cone in its lower end, but it is directed point upward and inside the container with small bores about its base circumference where it is attached to the cylinder and communicates with the lumen of the carrying tube. The other, upper end of the cylinder is closed by a stopper having ½ cm small-diameter tube 120 cm. long passing through it so that its lumen is connected to the lumen of the cylinder. The other, lower end of the carrying tube is again connected to an air pump. Any type of air pump may be used such as, for example, an insecticide sprayer pump. In use, from air the pump passes into the carrying tube, from the carrying tubes into container, through the pollen in the container into the stopper-held tube in the top of the container and then to the female flower, entraining some of the pollen from the container.

The Osamah Date Palm Pollinator is the same as the Mosa'ab, with two differences. First it has a 100 cm. long tube extending vertically form the open end of the horizontal tube. Its action is to take the pollen to the female flowers. Second, it has an electric air pump on the other, lower end of the carrying tube in place of the bulb pump previously described. The electric pump works on two, dry, 1.5 volt batteries to give enough low-pressure air for pollination work.

In all three of Applicant's prior pollinators, a mix of one part extracted pollen to 10 parts of fine flour is usable in the container.

The disadvantages of Mosa'ab pollinator are slow discharge of the pollen mixture, linking in the leaves and leaflets of the female palm tree too easily and the possibility of clumping of the flour mixture inside it. Its advantages are its light weight, that it does not need compressed air, and that it can reach to 12 m. high.

The disadvantages of the Mahmood Pollinator, are that it needs repeated pumping and that the big torque of tree contact with the upper, stopper-held, small tube can break it, because it cannot bend. Its advantages very rapid (fastest) discharge of the pollen mixture, that it can reach to 14 m. high, that it will not link in the leaves and leaflets of the female palm tree, that it is more economical in its use of the pollen mixture and that the pollen mixture does not clump inside it.

The disadvantages of the Osamah Pollinator are that it is too easily blocked by clumps of the pollen mixture and that its output of the pollen mixture is irregular. Its advantages are that it does not need repumping because it works on a battery and that it does not link in leaves and leaflets of the female palm tree.

All of applicant's prior pollinators have a further great advantage in that each can be carried easily by the hand between the trees and does not need big, difficult, additional machinery. Also, they have the air power from below and the pollen in the opposite, upper end. That means no loose pollen in the long carrying tube and no heavy part in the upper end. (If the diameter of the carrying tube is 3 cm, this means a volume in 10 m of about 7000 cc. This means a loss from use of 7000 cc of pollen saturated air if the pollen were air-entrained at the lower end of the carrying tube. Such substantial pollen loss is shown to be realistically avoided by comparison to the 95 cc. volume of the small-diameter tube of the Mahmood Pollinator.)

If the upper, pollen-discharging end carried the air-pumping power, the pollinator would become heavy and very difficult to use (A 10 m. carrying tube gives a very big torque with any weight on its upper end.)

It is, therefore, an object of the invention to provide a plant duster and, more particularly, a duster for date palm pollination which avoids at least some of the disadvantages and retains most of the advantages of those described.

BRIEF DESCRIPTION OF THE DRAWINGS

Prior and preferred embodiment of date palm pollinators which illustrate, but do not limit the invention are shown in the drawings, wherein;

FIG. 4 is an elevation of the pollinator of the invention, partly broken away;

FIG. 5 is an elevation of a portion of the pollinator of the invention not shown in FIG. 4;

FIG. 6 is an enlarged elevation of a portion of the portion of the pollinator shown in FIG. 5;

FIG. 7 is an enlarged elevation of a portion of the pollinator of FIG. 4; and

FIG. 8 is an elevation of a portion of another pollinator of the invention.

DESCRIPTION OF THE PREFERRED EMBODIMENTS

Figures 1, 2, 3:
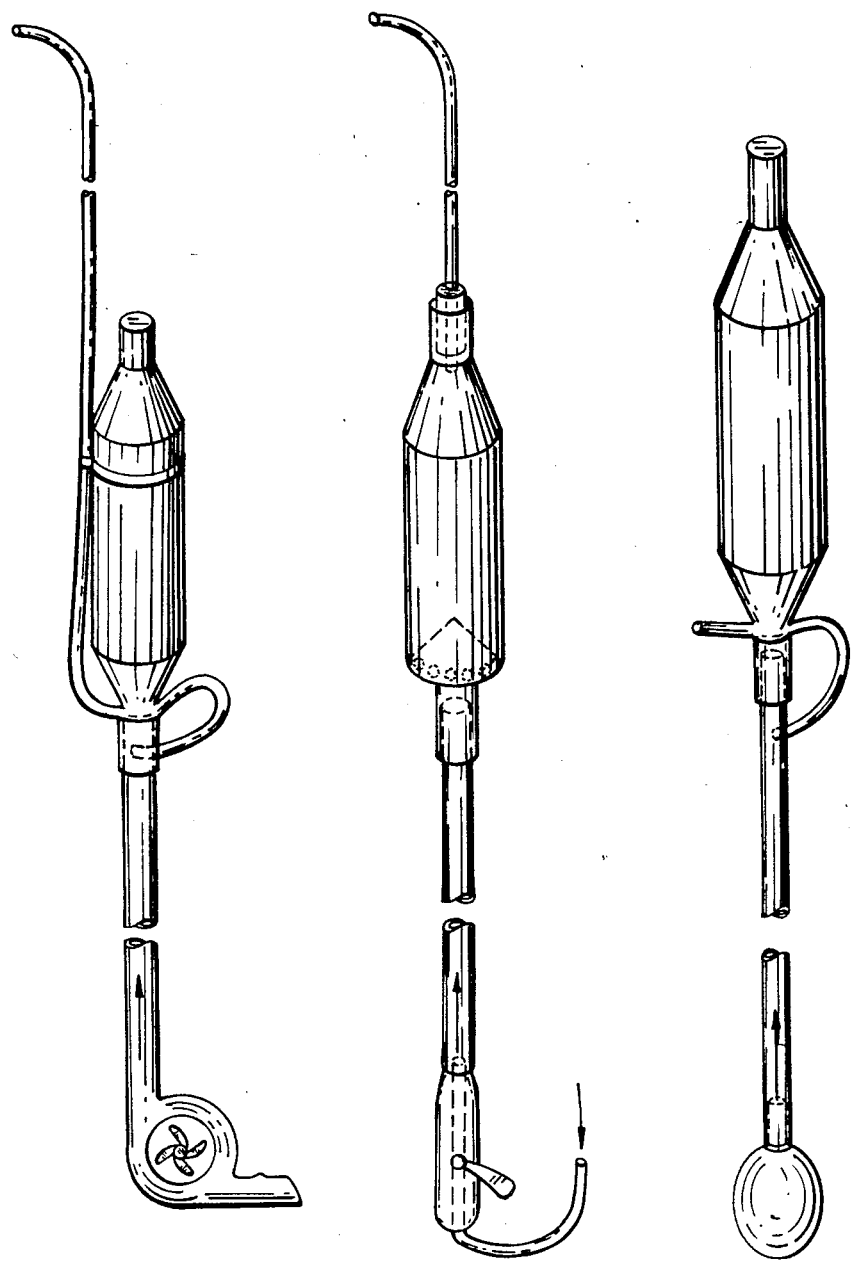
FIG. 1 is an elevation of the Mosa'ab Pollinator, partly broken away.
FIG. 2 is an elevation of the Mahmood Pollinator, partly broken away.
FIG. 3 is an elevation of the Osamah Pollinator, partly broken away.

Based on knowledge of the art, the design of the preferred pollinator embodiment of FIG. 4 is, hopefully, a step toward perfection. In a design similar to that of the Mahmood Pollinator previously described, an uppermost, pollen-dispersing, small-diameter tube 23 at one end of the pollinator enters a container 20 for pollen or a pollen-mixture through a rubber stopper 19 to make it flexible. Also, the container 20, which is cylindric, is longer than in the Mahmood Pollinator to give enough space for air/pollen powder mixing. Also, the connection of the container 20 to one end of the long carrying tube 28 is improved. The other, lower end of the carrying tube is connected to a battery-operated pump 33, as in the Osamah Pollinator, but with slightly increased air pressure and a prosthesis 40 for blowing into the pump 33 by mouth. These different measures give all the benefits of all the prior, described pollinators and get rid their disadvantage as much as possible. Many of the modifications make it much better.

More specifically, the preferred date palm pollinator has a cylinderic container 20 of 5 cm. diameter and 20 cm. length. Its upper end is a truncated cone 21 connected to a 2 cm. diameter tube 22, 2cm. long, where the rubber stopper 19 fixes in an aluminum tube 23 of 0.7 cm. inside diameter and 120 cm. length. This penetrates the stopper 14 to connect its lumen to the container 20. The lower end of the cylinder 20 is connected to two cones 24, 26. One, 24 directed upwards, towards the small-diameter tube 23, is 3 cm. high and has small pores 25 of ½ mm diameter about its base attachment to the cylinder. The second cone 26 is directed downward. It is truncated, like cone 21. It is connected to a tube 27 which is 3 cm. long and of 1 cm. diameter. The tube 27 has threads tobe screwed on to the upper end of the carrying tube 28. This head is the same of that of Mahmood Pollinator, but with many differences (1) The rubber stopper 19 connecting the small tube 23 to the upper end of the container gives its flexibility to the connection to prevent transmission of direct shock from contact of the leaves of the tree with the small tube 23 upon movement in use.

(2) The length of the cylinder 20 is such that it need not be filled with pollen mixture more than half to give enough space for air/pollen mixture mixing without clumps.

(3) The lower-end cone connection of the container 20 carrying tube 28 gives the container more stability and makes its connection stronger.

(4) The screw threads on the tube 27 on the lower end of the container makes disconnection and reconnection of the container 20 to a first section of the carrying tube 28 more practical.

The carrying tube 28 is the same graduated tube of the Mosa'ab Pollinator, only sectioned. Each section made from aluminum of 1 mm thickness. The carrying tube sections start with a 1 cm. outside diameter which increases by 6 mm for each of several similar sections (not shown) downward therefrom. Each section is 180 cm. long, except for the last section which step is shorter. The first section is 1 cm. diameter and 180 cm. long and the lowest, last will be 4.6 cm outside diameter and 150 cm. long.

The connections 29 between the carrying tube sections are of layers of hard plastic covering one, upper end of each tube section (except the first one). Its upper margin 30 continues as expanded area and is grooved as seen in the drawing to receive the next section, as on shortening the tube. The connection 29 is 7 cm. long and gives more stability and air tightness. The lower end of each tube has an expanded ring 31 which increases the diameter 1.2 mm. This gives 0.4 mm from each side to connect the carrying tube sections sliding by and easily. In the lower end of the plastic connections, there is small expansion 32 to receive the expanded area of the next tube. The connection 29 is an improvement to the carrying tube of Mosab'ab Pollinator. The total length of the pollinator with six pieces of the tube will be 10 m. This means it pollinates all date Palms after adding 2 m for the maximum reach of the human hand holding it. The plastic connections 29 are also insulators to prevent electric shock through the tube, which may occur. The elongation the carrying tube by 1.5 m for each step gives enough range to cover different heights of the trees with the great benefit of giving the smallest weight for the best stability for each and gives good dynamicity for the passing of air upward. The carrying tube sections also can be carried easily without bending.

The third part of the pollinator is the air pump 33. It is the same as that of Osamah Pollinator, but it gives a higher air pressure as needed by this pollinator. It consists of a cylinder 40 cm. long. Its lower part contains three, dry-type 1.5 V big batteries 34. Just above these is a motor 35 which rotates the air pump (air blower) 36 in a way that takes in air through openings 37 just around the motor to cool it and pushes the the from its center to the periphery of the tube to go up the center which open to the container 20. This pump part or housing 33 connects to the inside of carrying tube 28 at ring 31 with screw threads to be easily disconnected. For this, the upper end at 38, which goes inside the carrying tube 28, consists of short tubes, one inside the other, the same size as the lower, ring ends of the tubes of the carrying tube sections. In this area the end of the tube will be fixed on twisting (as seen in the drawing). The pressure needed to allow air to pass through the pollen is about 10 cm. water (10 Gm/Sq. Cm.). This pressure is easy to get with a flow of about 20 L. per minute. The electric switch buttons 39 for the pump are 15 cm. from its lower end.

In another embodiment (FIG. 8), a tubular housing **33*a* replaces the pump housing on the lower end of the carrying tube. It is connected to one end of a flexible tube 40 of 1 cm. inner deameter and 60 cm. length, with its opposite, lower end having a mouthpiece 41** for use by the mouth. This may be used for emergency or cheap operation, i.e. in place of the pump.

In this third part, we modify the air pump to be slightly stronger and we modify its upper end and the arrangement of the motor to be as a continuation of the carrying tube sections and easily disconnected therefrom.

From all this, we get the following results:

(1) Light weight;

(2) Easy carrying by one hand for jumping over the channels between the trees.

(3) Because it needs no heavy machinery, it is very easy to use.

(4) Very cheap, especially when used by mouth.

(5) Properly protected from shock.

(6) In general, it is not an electrical conductor.

(7) It is long enough to cover most date palms.

(8) Light upper-parts end easily elongated to make it easy to apply.

(9) Pollen does not clump and is well distributed to make it very economic in pollination.

(10) It is not linked in the leaves and leaflets easily, because the end tube only goes between the leaves and leaflets.

(11) It gives the best results in pollination because there is no stream of air from the pollinator after the pollen to push the pollen away from the flowers.

(12) The use of dry batteries makes it more applicable.

RESULTS OF APPLICATION (1) One worker pollinates 500 date palms daily by blowing by mouth.

(2) No difference in the quantity of the pollen used, in the manual type and this type.

(3) 15% improvement in the fertilized date with 10% improvement in the weight of the fruit.

(4) The cost of pollination of one date palm reduces to 16% of the manual (1250 fils for manual and 200 fils by the pollinator described, for example).

I claim:

1. A plant pollen duster, comprising:
a small tube for dispensing dust;
a container for the dust to be dispensed;
a rubber stopper in one end of the container and about one end of the small tube which thereby communicates with the container for receiving the dust;
a truncated, hollow cone having one end on the other end of the container for communicating with the dust therein;
a threaded tube on the other end of the truncated, hollow cone;
air-passing means in the cone for passing pumped air into the container and for preventing dust from the container from entering the threaded tube;
a first carrying tube section for threaded connection to the threaded tube at one end and having an enlargement about the other end;
at least one carrying tube section in a graduated diameter the further carrying tube section having an enlargement about one end and an expandable connection about the other end for releasibly receiving the enlargement of the first carrying tube section;
a last carrying tube section having an expandable connection on one end for releasibly receiving the enlargement of the further carrying tube and threads on the other end;
a housing having threads on one end for connection to the threads on the last carrying tube section; and
a tube connected to the housing at one end and having a mouthpiece on the opposite end for blowing air from the mouthpiece through the carrying tube sections into the container for dispensing the dust therefrom.

2. The plant duster of claim 1, wherein the expandable connections are formed from electrically insulating material for electrically insulating connected carrying tube sections from each other.

3. A plant pollen duster, comprising:
a small tube for dispensing dust;
a container for the dust to be dispensed;
a rubber stopper in one end of the container and about one end of the small tube which thereby communicates with the container for receiving the dust;
a truncated, hollow cone having one end on the other end of the container for communicating with the dust therein;
a threaded tube on the other end of the truncated, hollow cone;
air-passing means in the cone for passing air into the container and for preventing dust from the container from entering the threaded tube;
a first carrying tube section for threaded connection to the threaded tube at one end and having an enlargement about the other end;
at least one further carrying tube section in a graduated diameter, the further carrying tube section having an enlargement about one end and an expandable connection about the other end for releasibly receiving the enlargement of the first carrying tube section;
a last carrying tube section having an expandable connection on one end for releasibly receiving the enlargement of the further carrying tube and threads on the other end;
a housing having threads on one end for connection to the threads on the last carrying tube section; and
a battery-operable air pump in the housing for pumping air through the carrying tube sections to the container, whereby to entrain the dust therein and dispense the entrained dust through the small tube.

4. The plant duster of claim 3, wherein the expandable connections are formed from electrically insulating material for electrically insulating connected carrying tube section from each other.

* * * * *